United States Patent
Miguelino et al.

(10) Patent No.: US 11,805,788 B2
(45) Date of Patent: Nov. 7, 2023

(54) ORAL CARE COMPOSITIONS COMPRISING A FLAVOR SYSTEM

(71) Applicant: Colgate-Palmolive Company, New York, NY (US)

(72) Inventors: Michelle Miguelino, Somerset, NJ (US); Fusong Sun, Martinsville, NJ (US); Veronica Semeghini, Whitehouse Station, NJ (US); Mania Bankova, Highland Park, NJ (US); Victoria Yeung, Livingston, NJ (US); Tracy Bariexca, Hoboken, NJ (US); Catalina Monroy, Princeton, NJ (US); Cajetan Dogo-Isonagie, Mount Laurel, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 18/091,950

(22) Filed: Dec. 30, 2022

(65) Prior Publication Data

US 2023/0210129 A1 Jul. 6, 2023

Related U.S. Application Data

(60) Provisional application No. 63/295,148, filed on Dec. 30, 2021.

(51) Int. Cl.
*A23G 4/10* (2006.01)
*A23G 3/42* (2006.01)

(52) U.S. Cl.
CPC ............... *A23G 4/10* (2013.01); *A23G 3/42* (2013.01); *A23V 2002/00* (2013.01)

(58) Field of Classification Search
CPC ......... A23G 4/10; A23G 3/42; A23V 2002/00
See application file for complete search history.

(56) References Cited

U.S. PATENT DOCUMENTS

| | | |
|---|---|---|
| 5,004,595 A | 4/1991 | Cherukuri et al. |
| 6,261,540 B1 | 7/2001 | Nelson |
| 6,932,982 B2 | 8/2005 | McIver et al. |
| 10,299,998 B2 | 5/2019 | Fei et al. |
| 10,709,646 B2 | 7/2020 | Robbins et al. |
| 10,716,741 B1 | 7/2020 | Yuan et al. |
| 10,716,742 B2 | 7/2020 | Yuan et al. |
| 10,729,626 B2 | 8/2020 | Potnis et al. |
| 10,744,075 B2 | 8/2020 | Dogo-Isonagie et al. |
| 10,758,462 B2 | 9/2020 | Yuan et al. |
| 11,166,890 B2 | 11/2021 | Dogo-Isonagie et al. |
| 11,229,588 B2 | 1/2022 | Plata et al. |
| 2015/0019648 A1 | 1/2015 | Harris et al. |
| 2020/0138682 A1 | 5/2020 | Galiyara et al. |

FOREIGN PATENT DOCUMENTS

| | | |
|---|---|---|
| WO | 2006/086061 | 8/2006 |
| WO | 2006/127070 | 11/2006 |
| WO | 2012/145611 | 10/2012 |

OTHER PUBLICATIONS

Anais Pitto-Barry & Nicolas P. E. Barry, "Pluronic block-copolymers in medicine: from chemical and biological versatility to rationalization and clinical advances," Polymer Chemistry 2014, 5, 3291.
Andrew M. Bodratti & Paschalis Alexandridis, "Formulation of Poloxamers for Drug Delivery," Journal of Functional Biomaterials 2018, 9, 11.
Eleanora Russo & Carla Villa, "Poloxamer Hydrogels for Biomedical Applications," Pharmaceutics 2019, 11, 671.
International Search Report and the Written Opinion of the International Searching Authority issued in International Application PCT/US2022/054377 dated May 10, 2023.

*Primary Examiner* — Trevor Love

(57) ABSTRACT

The present disclosure provides low-water oral care compositions comprising a whitening agent and a flavor system encapsulating one or more flavor ingredients, wherein the flavor system provides improved taste to the consumer, masking the negative taste attributes of the whitening or oxidizing agents, and is also believed to be able to improve the flavor stability over the life of the product, and methods of using the same.

20 Claims, No Drawings

ORAL CARE COMPOSITIONS COMPRISING A FLAVOR SYSTEM

CROSS-REFERENCE TO RELATED APPLICATIONS

This application claims priority to, and the benefit of, U.S. Provisional Application No. 63/295,148, filed on Dec. 30, 2021, the contents of which are hereby incorporated by reference in its entirety.

FIELD OF THE INVENTION

The disclosure provides low-water oral care compositions comprising a flavor system, wherein the flavor system comprises a carrier matrix for encapsulating one or more flavor(s) ingredients, and wherein the carrier matrix comprises one or more flavor ingredients. In one aspect, the carrier matrix comprises a protective coating layer. In one aspect the protective coating layer comprises maltodextrin and/or a gum arabica. In one aspect the flavor system can comprise both encapsulated and non-encapsulated (e.g., liquid) flavor ingredients. In one aspect, the oral care compositions comprising the flavor system are anhydrous or low water formulations (e.g., from 0.1%-4% by wt. of water), wherein the composition further comprises a whitening agent. Preferably, the oral care compositions comprise a whitening agent, and one or more flavors which are susceptible to oxidation or oxidative degradation, and the flavor system protects the flavor ingredients from oxidation or degradation. This results in a significant improvement in the taste of the compositions and the perception of whitening efficacy. Methods for making and using the oral care compositions are also described herein.

BACKGROUND OF THE INVENTION

Various whitening agents (e.g., hydrogen peroxide and peroxymonosulfate) used in oral care composition are known to have disadvantages regarding negative taste attributes such as: bitterness, metallic taste, chlorine-like taste, irritation, etc. Moreover, being oxidizing agents, the same whitening agents may be chemically incompatible with many ingredients that are used to provide flavor to an oral care composition and create a pleasant tasting product. Flavor molecules often have oxidizable functional groups, such as alcohols and double bonds, and these functional groups can be destroyed by strong oxidizing agents, especially during prolonged storage in compositions. Therefore, there is a significant challenge in creating a stable and pleasant flavor system that is also compatible with these oral compositions.

Additionally, whitening toothpastes generally need to be used regularly in order for them to be effective. Flavors and sweeteners are an integral part of creating an appealing product that encourages regular use. Without these ingredients, brushing compliance is difficult and the user is unlikely to fully attain the potential whitening benefit. Moreover, flavor formulation can be complicated and many components in flavors can be susceptible to oxidation. In turn, the oxidation can impact the overall stability of the flavor over the shelf life of the composition and can generate off notes that are unpleasant to the consumer. Flavoring oral care compositions that contain strong oxidizing agents, e.g., hydrogen peroxide and peroxymonosulfate, can create further challenges as these oxidation reactions occur rapidly and continue to occur over the lifetime of the product.

Another challenge can be that oral care compositions that contain whitening agents may be anhydrous or contain low water. The drawback to this approach, however, is that anhydrous or low water oral care compositions can be difficult to formulate with desired rheological properties and in such a way that they are palatable to the user.

Off-notes are in particular a challenging problem for oral whitening compositions. Not only must the generation of off-notes due to the oxidation of ingredients in the composition be avoided (including degradation products of the flavor ingredients), but the inherently off-taste of the whitening agent and other ill-tasting ingredients (such as some polymers and surfactants) must be masked as well by the flavor system.

Accordingly, there is a need to identify a flavoring system for whitening oral care compositions, which is acceptable over the life of the product and can present an enjoyable taste to the consumer, while also masking the negative taste attributes that may arise whitening agents.

SUMMARY OF THE INVENTION

In one aspect, the application provides for low-water or anhydrous oral care compositions comprising a flavor system, wherein the flavor system comprises a carrier matrix for encapsulating one or more flavor ingredients and wherein the carrier matrix comprises one or more flavor ingredients. In one aspect, the flavor system of the oral care compositions comprises an encapsulation carrier matrix, wherein the matrix comprises a protective coating layer. In one aspect the protective coating layer comprises maltodextrin and/or a gum arabica. In one aspect the carrier matrix comprises a protective layer that encapsulates one or more flavor ingredients as droplets which are then distributed upon use of the composition in the oral cavity.

Without being bound by theory, the carrier matrix described herein can be used to encapsulate an active compound (e.g., flavor ingredient) wherein the active compound is encapsulated with a protective wall material. In this aspect, the carrier matrix may be used to encapsulate and deliver flavor ingredients and protect them against reaction with the remaining formulation or environment. In one aspect, the oral compositions described here do not contain an aqueous solvent (e.g., so the carrier matrix does not degrade) and the protective coating layer of the carrier prevents or reduces the oxidation of the flavor by separating the flavor from the oxidizing agents, therefore improving the stability and decreasing the generation of off-tastes caused by the degradation products. Consequently, in one aspect, the flavor system comprises a liquid flavor (i.e., not encapsulated) used in conjunction with a carrier matrix that encapsulates one or more flavors and is able to provide an enjoyable or improved taste to the consumer, masking the negative taste attributes of the whitening or oxidizing agents, and is believed to be able to improve the flavor stability over the life of the product.

In one aspect, the carrier matrix can be modified to control the release of the flavor ingredient to enhance the user experience. In this aspect, the carrier matrix may be designed to dissolve, break, and/or release the encapsulated flavor ingredient through product usage. In another aspect, the carrier matrix can comprise a protective coating layer, wherein the protective coating layer contains gum arabica or maltodextrin which are designed to release the encapsulated flavor ingredient. Indeed, in one aspect, the carrier matrix is water soluble and is useful for releasing the encapsulated flavor ingredient when the oral care composition is used in the oral cavity via brushing or through interaction with saliva in the oral cavity.

In one aspect, aqueous formulations or environments (e.g., the oral cavity upon use of a product) can present challenges to the stability of the carrier matrix the comprises a protective coating layer for encapsulating the one or more flavor ingredient(s). For example, the carrier can be weakened or broken by the aqueous solvents. In turn, this may result in the migration or complete release of the encapsulated flavor ingredient from the carrier matrix into the composition prior to when it would be considered optimal to deliver the flavor ingredient.

Accordingly, in one aspect, the oral care compositions of the disclosure are low-water oral care compositions comprising one or more whitening agents and a flavor system, wherein the flavor system comprises a carrier matrix that comprises one or more flavor ingredients encapsulated within the protective coating layer of the carrier. In this aspect, the oral care composition has the advantage of being able to potentially stabilize strong oxidizing whitening agents. In some aspects, the low water composition comprises a flavor system, wherein the flavor system comprises one or more non-encapsulated liquid flavors and a carrier matrix, wherein the carrier matrix comprises a protective layer that encapsulates one or more additional flavor ingredients.

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight relative to the total composition. The amounts given are based on the active weight of the material.

Open terms such as "include," "including," "contain," "containing" and the like mean "comprising." In this description, unless otherwise stated, the use of the singular also includes the plural. For example, "a lubricant" also comprehends the case where more than one lubricant is used.

"About" means plus or minus 20% of the stated value. Thus, for example, "about 5%" means from 80% to 120% of 5%, or 4.0% to 6.0%, inclusive of the end values of the range.

In one aspect, the disclosure provides a low-water oral care composition (Composition 1.0) comprising:
 (a) a flavor system, wherein the flavor system comprises a carrier matrix for encapsulating one or more flavor ingredient(s), and wherein the carrier matrix comprises a protective coating layer that encapsulates the flavor ingredient(s) (e.g., wherein the protective coating layer comprises maltodextrin or gum arabica); and
 (b) whitening agent (e.g., potassium peroxymonosulfate); and
wherein the low-water oral care composition comprises less than 4% water, by weight of the total composition, e.g., from 0% to 4% water, or from 0.05% to 4% water, by weight of the total composition.

For example, the disclosure provides embodiments of Composition 1.0 as follows:
 1.1. Composition 1.0, wherein the composition comprises less than 4%, or less than 3%, or less than 2%, or less than 1% water, by weight of the total composition;
 1.2. Composition 1.1, wherein, the composition comprises from 0% to 4% water, by weight of the composition, e.g., from 0.1% to 4%, or from 0.1% to 3%, or from 0.1% to 2%, or from 0.1% to 1% water, by weight of the total composition;
 1.3. Any of the preceding compositions, wherein the composition is anhydrous (e.g., about 0% water, by weight of the total composition);
 1.4. Any of the preceding compositions, wherein the composition comprises the flavor system in an amount of 0.05% to 5%, by weight of the total composition;
 1.5. Any of the preceding compositions, wherein the flavor system comprises one or more flavor ingredients, e.g., wherein the flavor ingredient(s) are each present in an amount of 0.1 to 5%, or 0.5 to 5%, or 1 to 5%, or 2 to 5%, or 2 to 3%, or 0.1 to 3%, or 0.1 to 2%, or 0.1 to 1%, or 0.1 to 0.5%, or 0.1 to 0.3%, or 1 to 4%, or 1 to 3%, or 1 to 2%, or 1 to 1.5%, or 2 to 4%, or 3 to 5%, or 3 to 4%, by weight of the total composition;
 1.6. Any of the preceding compositions, wherein the carrier matrix comprises a protective coating layer, wherein the protective coating layer comprises agar (e.g., agar-agar) and a carbohydrate material selected from the group consisting of: maltodextrin, corn syrup, a chemically modified starch, a hydrogenated starch hydrolysate, succinylated starch, hydrolyzed starch, and combinations thereof,
 1.7. Composition 1.6, wherein the protective coating layer of the carrier matrix comprises agar (e.g., agar-agar) and maltodextrin (e.g., maltodextrin with a dextrose equivalent of at least 18);
 1.8. Composition 1.7, wherein the maltodextrin is the primary carbohydrate material of the carrier matrix (e.g., greater than 50 weight % of the carrier matrix) or is present as an admixture with any of the following sugars selected from: sucrose, glucose, lactose, fructose, sorbitol, isomalt, ribose, levulose, mannitol, lactitol, xylitol, dextrose, maltitol, xylose, galactose, pentatol, pentose, arabinose and combinations thereof,
 1.9. Composition 1.8, wherein the maltodextrin is present as an admixture with sucrose;
 1.10. Any of the preceding compositions, wherein the protective layer of the carrier matrix comprises agar, a carbohydrate material (e.g., maltodextrin) and an emulsifier (e.g., soya lecithin and citric acid esters of fatty acids);
 1.11. Any of the preceding compositions, wherein the protective layer of the carrier matrix comprises maltodextrin, agar and an emulsifier (e.g., soya lecithin) and optionally sucrose;
 1.12. Composition 1.11, wherein the maltodextrin is present from 70% to 85% (e.g., about 81%) by weight relative the dry weight of the carrier matrix, wherein the emulsifier (e.g., soya lecithin) is present from 0.25 to 2% (e.g., about 1%) by weight relative to the dry weight of the carrier matrix, and wherein the agar is present from 0.25% to 2% (e.g., about 1.5%) by weight relative to the dry weight of the carrier matrix;
 1.13. Composition 1.12, wherein the protective layer comprises maltodextrin, agar, an emulsifier and sucrose, wherein the maltodextrin is present from 35% to 50% (e.g., about 43% to about 44%) by weight relative the dry weight of the carrier matrix, wherein the emulsifier (e.g., soya lecithin) is present from 0.25 to 2% (e.g., about 0.5%) by weight relative to the dry weight of the carrier matrix, wherein the sucrose is present from 35% to 50% (e.g., about 43% to about 44%) by weight relative the dry weight of the carrier matrix, and wherein the agar is present from 0.25% to 2% (e.g., about 1%) by weight relative to the dry weight of the carrier matrix;

1.14. Any of the preceding compositions wherein, the protective coating layer comprises gum arabica;

1.15. Any of the preceding compositions, wherein the flavor system comprises a carrier matrix that comprises FLEXAROME and/or DURAROME (commercially available from Firmenich International, SA), and wherein the FLEXAROME and/or DURAROME encapsulates and delivers the one or more flavor ingredient(s);

1.16. Any of the preceding compositions, wherein the flavor system comprises one or more non-encapsulated liquid flavor ingredients and a carrier matrix that encapsulates one or more additional flavor ingredient(s);

1.17. Any of the preceding compositions, wherein the whitening agent comprises hydrogen peroxide and/or potassium peroxymonosulfate;

1.18. Composition 1.17, wherein the whitening agent comprises potassium peroxymonosulfate;

1.19. Composition 1.18, wherein the potassium peroxymonosulfate is provided as a triple salt of potassium peroxymonosulfate, potassium hydrogen sulfate and potassium sulfate, optionally wherein the triple salt comprises about 45%-50% by weight of potassium peroxymonosulfate, e.g., 47% or 49% by weight of potassium peroxymonosulfate;

1.20. Any of the preceding compositions, wherein the composition comprises the potassium peroxymonosulfate in an amount of 0.01% to 10% by weight of the composition, e.g., 0.01 to 5%, or 0.05% to 5%, or 0.1% to 5%, or 0.5% to 3%, or 0.5% to 2.5%, or 0.5% to 2%, or 0.5% to 1.5%, or 0.75% to 1.2 5%, or 1% to 5%, or 1% to 4%, or 1% to 3% or 1% to 2%, or 1.5% to 3%, or 2% to 3%, or 1.5% to 2%, or 2% to 2.5%, or about 0.5%, or about 1%, or about 1.5%, or about 2%, or about 2.5%, by weight of the composition.

1.21. Any of the preceding compositions, wherein the inorganic peroxymonosulfate salt is not particulated (e.g., not granulated);

1.22. Any of the preceding compositions, wherein the composition does not comprise any of hydrogen peroxide, urea peroxide, peroxide salts (e.g., sodium peroxide, potassium peroxide, lithium peroxide, calcium peroxide), peroxy acids (e.g., peroxyacetic acid, peroxybenzoic acid, or salts or derivatives thereof), organic peroxides (e.g., urea hydrogen peroxide, glyceryl hydrogen peroxide, peroxy esters, diacyl peroxides, monoperoxyphthalate, or salt thereof), perborate salts, persilicate salts, percarbonate salts, chlorinated oxidizing agents (e.g., hypochlorite salts, chlorite salts, chlorate salts, perchlorate salts, chlorine dioxide), or peroxydisulfuric acid or peroxydisulfate salts;

1.23. Any of the preceding compositions, wherein the whitening agent comprises potassium peroxymonosulfate (MPS), and wherein the MPS is the only oxidizing agent present in the Composition;

1.24. Any of the preceding compositions, wherein the composition comprises calcium pyrophosphate and/or the insoluble sodium metaphosphate in an amount of 22% to 60%, or 22% to 50%, or 22% to 40%, or 22% to 35%, or 25% to 60%, or 25% to 50%, or 25% to 40%, or 25% to 35%, or 25% to 30%, or 21% to 30%, or 22% to 30%, or 22.5% to 27.5%, or 23% to 27%, or 24% to 26%, or about 25%, by weight of the composition;

1.25. Any of the preceding compositions, wherein the composition comprises a polyoxyethylene/polyoxypropylene triblock copolymer, and wherein the triblock copolymer has the formula

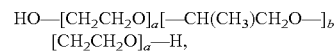

wherein a is an integer between 1 and 30, b is an integer between 10 and 60.

1.26. Composition 1.25, wherein in said formula, a is an integer between 5 and 20, and b is an integer between 10 and 40;

1.27. Composition 1.26, wherein in said formula, a is an integer between 10 and 15, and b is an integer between 10 and 20;

1.28. Composition 1.27, wherein in said formula, a is an integer between 10 and 12 (e.g., 11), and b is an integer between 15 and 20 (e.g., 16);

1.29. Any of Compositions 1.25-1.28, wherein the polyoxyethylene/polyoxypropylene triblock copolymer has an average molecular weight of 1000 to 7000 Daltons, e.g., 1000 to 6000 Daltons, or 1000 to 5000 Daltons, or 1000 to 4000 Daltons, or 1000 to 3000 Daltons, or 1000 to 2000 Daltons, or 1500 to 3000 Daltons, or 1500 to 2000 Daltons, or 1800 to 2000 Daltons, or about 1900 Daltons, optionally wherein said average molecular weight is a number average molecular weight or a weight average molecular weight;

1.30. Composition 1.29, wherein the polyoxyethylene/polyoxypropylene triblock copolymer is Pluronic L35;

1.31. Any of Compositions 1.25-1.30, wherein the composition comprises the polyoxyethylene/polyoxypropylene triblock copolymer in an amount of 22% to 60%, or 22% to 50%, or 22% to 40%, or 22% to 35%, or 25% to 60%, or 25% to 50%, or 25% to 40%, or 25% to 35%, or 27% to 33%, or 28% to 32%, or about 30%, or about 31%, by weight of the composition;

1.32. Any of the preceding compositions, wherein the composition further comprises one or more of polyvinylpyrrolidone, polyethylene glycol/polypropylene glycol random copolymer, polyethylene glycol, polyphosphates (e.g., alkali metal polyphosphates), and surfactants (e.g., anionic and/or zwitterionic surfactants);

1.33. Any of the preceding compositions, wherein the Composition further comprises polyvinylpyrrolidone;

1.34. Composition 1.33, wherein the polyvinylpyrrolidone is cross-linked polyvinylpyrrolidone;

1.35. Any of Compositions 1.32-1.34, wherein the polyvinylpyrrolidone is not complexed with or combined with hydrogen peroxide;

1.36. Any of Compositions 1.32-1.34, wherein the composition comprises the polyvinylpyrrolidone ("PVP") in an amount of 1% to 50%, or 1% to 40%, or 1% to 30%, or 1% to 25%, or 1% to 22%, or 1% to 20%, or 1% to 18%, or 1% to 15%, or 1% to 12%, or 1% to 10%, or 1% to 8%, or 1% to 6%, or 3% to 15%, or 3% to 12%, or 3% to 10%, or 3% to 8%, or 3% to 6%, or 4% to 8%, or 4% to 6%, or about 5%, by weight of the composition;

1.37. Any of the preceding compositions, wherein the composition further comprises a polyethylene glycol/polypropylene glycol random copolymer (PEG/PPG copolymer);

1.38. Composition 1.37, wherein the PEG/PPG random copolymer has an average molar ratio of ethylene glycol units to propylene glycol units of about 75-150 EG to 45-95 PG, or about 95-135 EG to 50 to 80 PG, or about 105-125 EG to 55-75 PG, or about 110-120 EG to 60-70 PG, or about 116 EG to 66 PG (i.e., PEG/PPG 116/66);

1.39. Composition 1.37 or 1.38, wherein the PEG/PPG random copolymer is Pluracare L1220;

1.40. Any of Compositions 1.37-1.39, wherein the composition comprises the PEG/PPG random copolymer in an amount of 1% to 50%, or 1% to 40%, or 1% to 30%, or 1% to 25%, or 1% to 20%, or 1% to 18%, or 1% to 15%, or 1% to 12%, or 1% to 10%, or 6% to 40%, or 6% to 30%, or 6% to 25%, or 6% to 20%, or 6% to 15%, or 6% to 10%, or 8% to 30%, or 8% to 25%, or 8% to 20%, or 8% to 15%, or 8% to 12%, or 10% to 30%, or 10% to 25%, or 10% to 20%, or 10% to 15%, or 10% to 12%, or about 10%, by weight of the composition;

1.41. Any of the preceding compositions, wherein the composition further comprises polyethylene glycol;

1.42. Composition 1.41, wherein the polyethylene glycol is selected from the group consisting of PEG-200, PEG-300, PEG-400, PEG-500, PEG-600, PEG-800, PEG-1000, PEG-1600, and PEG-2000;

1.43. Composition 1.42, wherein the polyethylene glycol is PEG 600;

1.44. Any of Compositions 1.41-1.43, wherein the composition comprises polyethylene glycol in an amount of 1 to 50%, or 1 to 40%, or 1 to 30%, or 1 to 25%, or 1 to 20%, or 1 to 18%, or 1 to 15%, or 5 to 40%, or 5 to 30%, or 5 to 25%, or 5 to 20%, or 5 to 15%, or 8 to 40%, or 8 to 30%, or 8 to 25%, or 8 to 20%, or 8 to 15%, or 10 to 30%, or 10 to 25%, or 10 to 20%, or 10 to 15%, or 12 to 25%, or 12 to 20%, or 12 to 15%, or about 12% (e.g., about 12.5%), by weight of the composition;

1.45. Any of the preceding compositions, wherein the composition further comprise one or more additional polymers, such as, any one or more of: polypropylene glycols, polysaccharides (e.g., cellulose derivatives, for example carboxymethyl cellulose, hydroxypropyl cellulose, hydroxypropyl methyl cellulose, ethyl cellulose, microcrystalline cellulose; or polysaccharide gums, for example xanthan gum, guar gum, or carrageenan gum, pectins, karaya gum); chitosans; dextrans; hyaluronic acid and sodium hyaluronates; synthetic anionic polymeric polycarboxylates, such as copolymers of maleic anhydride or acid with another polymerizable ethylenically unsaturated monomer, preferably methyl vinyl ether (e.g., copolymers in a 1:4 to 4:1 ratio of maleic anhydride/acid to methyl vinyl ether); polyphosphonic acids and polyphosphonates (i.e., polyphosphoesters); cross-linked carboxyvinyl copolymers; polyacrylic acid or polyacrylate polymers (e.g. carbomers); polyacrylamides, such as (2-hydroxypropyl)methacrylamide; other polyoxyethylene-polyoxypropylene copolymers (PEG-PPG) tri-block copolymers, such as poloxamer 105, 108, 122, 123, 124, 182, 183, 184, 185, 188, 212, 215, 217, 234, 235, 237, 238, 288, 333, 334, 335, 338, 402, 403, or 407); PEG-PPG tetrablock copolymers; other PEG/PPG random copolymers, such as PEG/PPG-38/8; polyamines; polyvinyl alcohols; polyoxazolines, such as poly(2-alkyl-2-oxazolines), e.g., methyl, ethyl, or isopropyl substituted polyoxazolines; and quaternary ammonium polymers;

1.46. Any of the preceding compositions, wherein the composition does not comprise any one or more of: polyacrylic acid or polyacrylate polymers (PAA), polyvinylpyrrolidone-vinyl acetate copolymers (PVP-VA), polyoxazoline polymers (PO), and mixtures thereof;

1.47. Any of the preceding compositions, wherein the composition comprises 30 to 70% by weight of polymers (e.g., PEG/PPG random copolymer, PEG/PPG triblock copolymer, PVP, and PEG), e.g., 30 to 60% by weight, or 40 to 60% by weight, or 50 to 60% by weight, or 55 to 60% by weight, or 55 to 59% by weight, or 58 to 59% by weight;

1.48. Any of the preceding compositions, wherein the composition further comprises a polyphosphate or an organic cyclic polyphosphate, such as an alkali metal pyrophosphate, an alkali metal tripolyphosphate, an alkali metal tetraphosphate, an alkali metal hexametaphosphate, an alkali metal insoluble metaphosphate, an alkali metal phytic acid salt, or a mixture thereof;

1.49. Composition 1.48, wherein the composition comprises a sodium or potassium pyrophosphate, a sodium or potassium tripolyphosphate, a sodium or potassium tetraphosphate, a sodium or potassium phytic acid salt, or a mixture thereof;

1.50. Composition 1.48, wherein the composition comprises tetrasodium or tetrapotassium pyrophosphate;

1.51. Composition 1.48, wherein the composition comprises disodium pyrophosphate or dipotassium pyrophosphate;

1.52. Composition 1.48, wherein the composition comprises tetrasodium pyrophosphate and disodium pyrophosphate;

1.53. Any of Compositions 1.48-1.52, wherein the composition comprises from 0.1 to 5% by weight of polyphosphates, e.g., 0.5 to 5%, or 1% to 5%, or 2% to 5%, or 3 to 5%, or 3.5% to 5%, or 4% to 5%, or 3.5% to 4.5%, or about 4% by weight of polyphosphates (e.g., about 3% tetrasodium pyrophosphate and about 1% disodium pyrophosphate);

1.54. Any of the preceding compositions, wherein the composition further comprises one or more surfactants, e.g., anionic surfactants, cationic surfactants, amphoteric, non-ionic, and/or zwitterionic surfactants;

1.55. Any of the preceding compositions, wherein the composition comprises a mixture of anionic and zwitterionic surfactants;

1.56. Any of the preceding compositions, wherein the composition comprises one or more anionic surfactants, and wherein the anionic surfactants are selected from: sodium lauryl sulfate, sodium laureth sulfate, sodium myreth sulfate, sodium lauroyl sarcosinate, sodium coconut monoglyceride sulfonates, sodium lauryl benzene sulfonate, sodium lauryl sulfoacetate, sodium N-methyl N-cocoyl taurate, sodium cocoyl isethionate, sodium dioctyl sulfosuccinate, and sodium cocomonoglyceride sulfate, and ammonium analogs thereof;

1.57. Any of the preceding compositions, wherein the composition comprises one or more zwitterionic surfactants, and wherein the surfactants zwitterionic surfactants are selected from: cocamidopropyl betaine, cocamidopropyl sultaine, cocamidopropyl hydroxysultaine, lauramidopropyl betaine, lauramidopropyl sultaine, lauramidopropyl hydroxysultaine, oleamidopropyl betaine, oleamidopropyl sultaine, oleamidopropyl hydroxysultaine, tallowamideopropyl betaine, tallowamidopropyl sultaine, tallowamidopropyl hydroxysultaine, lauryl betaine, lauryl sultaine, lauryl hydroxysultaine, lauryldimethylamine oxide, and myristamine oxide;

1.58. Any of the preceding compositions, wherein the composition comprises one or more cationic surfactants, and wherein the cationic surfactants are selected from: cetylpyridinium chloride (CPC), cetrimonium bromide, benzalkonium chloride, benzethonium chloride (1-hexadecylcarbamoyl-ethyl)-trimethylammonium halide, (1-hexadecylcarbamoyl-2-phenyl-ethyl)-trimethylammonium halide, 1-hexadecylcarbamoyl-1, 1-dimethyl-pyrrolidinium halide, and [2-(1H-indole-3-yl)-1-hexadecylcarbamoyl-ethyl)]-trimethylammonium halide, wherein said halide is optionally chloride, fluoride or bromide, or lauroyl arginine, ethyl lauroyl arginine ester hydrochloride, or disodium sebacoyl bis-lauramidolysine;

1.59. Any of the preceding compositions, wherein the composition comprises one or more non-ionic surfactants, wherein said non-ionic surfactants are selected from: cocomonoethanolamide, cocodiethanolamide, laurylamidopropyl dimethylamine oxide, myristylamidopropyl dimethylamine oxide, and decyl glucoside;

1.60. Any of the preceding compositions, wherein the composition further comprises sodium lauryl sulfate;

1.61. Any of the preceding compositions, wherein the composition further comprises cocamidopropyl betaine;

1.62. Any of the preceding compositions, wherein the composition further comprises a mixture of sodium lauryl sulfate and cocamidopropyl betaine;

1.63. Any of the preceding compositions, wherein the composition comprises 0.1 to 5% of surfactants, e.g., 0.5% to 5%, or 1 to 5%, or 1.5 to 5%, or 2 to 5%, or 3 to 5%, or 4 to 5%, or 1 to 4%, or 2 to 4%, or 3 to 4%, or 2 to 5%, or 3 to 5%, or 1 to 3%, or 2 to 3%, or 2 to 2.5%, or 2.5 to 3%, or 2.25 to 2.75%, or 2.25 to 2.5%, or about 2.3%, by weight of the composition;

1.64. Any of the preceding compositions, wherein the composition comprises any one or more surfactants in an individual amount of 0.1 to 5% of surfactants, e.g., 0.1% to 4%, or 0.1 to 3%, or 0.1 to 2.5%, or 0.1 to 2%, or 0.1 to 1.5%, or 0.1 to 1%, or 0.1 to 0.5%, or 1 to 4%, or 2 to 4%, or 1 to 3%, or 2 to 3%, or 1.5 to 2.5%, or 2 to 2.5%, or about 0.3% or about 2%, by weight of the composition;

1.65. Any of the preceding compositions, wherein the composition comprises 0.1 to 5%, or 1 to 5%, or 2 to 4%, or 1 to 3%, or 2 to 3%, or 1.5 to 2.5%, or 2 to 2.5%, or about 2%, of sodium lauryl sulfate, and 0.1 to 1%, or 0.1 to 0.5%, or about 0.3%, of cocamidopropyl betaine, by weight of the composition;

1.66. Any of the preceding compositions, wherein the composition comprises the anionic surfactant (e.g., sodium lauryl sulfate) and the zwitterionic surfactant (e.g., cocamidopropyl betaine) in a weight ratio of about 20:1 to 1:1, e.g., about 20:1 to 2:1, or about 15:1 to 3:1, or about 12:1 to 4:1, or about 10:1 to 5:1, or about 8:1 to 5:1, or about 7:1 to 5:1, or about 6:1;

1.67. Any of the preceding compositions, wherein the composition further comprises an antioxidant, e.g., selected from butylated hydroxyanisole, butylated hydroxytoluene, vitamin A, carotenoids, vitamin E, flavonoids, polyphenols, ascorbic acid, and mixtures thereof, 1.68. Composition 1.67, wherein the antioxidant is butylated hydroxyanisole, butylated hydroxytoluene;

1.69. Composition 1.67, wherein the antioxidant is butylated hydroxytoluene;

1.70. Any of Compositions 1.67-1.69, wherein the composition comprises one or more antioxidants in an individual amount of 0.001 to 1%, e.g., 0.01% to 0.5%, or 0.01 to 0.3%, or 0.01 to 0.1%, or 0.01 to 0.05%, or about 0.03%, by weight of the composition;

1.71. Any of the preceding compositions, wherein the composition further comprises a thickening agent, e.g., magnesium aluminum silicate, or fumed silica, optionally in an amount of 0.1 to 10% by weight of the composition, e.g., 1 to 10%, or 2.5 to 10%, or 3 to 10%, or 2.5 to 7.5%, or 3 to 8%, or 3 to 6%, or 3 to 5%, or about 4%, by weight of the composition;

1.72. Any of the preceding compositions, wherein the composition further comprises a fluoride source;

1.73. Composition 1.72, wherein the fluoride source is selected from sodium fluoride, sodium monofluorophosphate, and stannous fluoride, or mixtures thereof, 1.74. Composition 1.72 or 1.73, wherein the composition comprises 0.1 to 5% of a fluoride source(s) by weight of the composition, e.g., 0.5 to 5%, or 0.5 to 3%, or 0.5 to 2%, or 0.5 to 1%, or about 0.75%, by weight of the composition;

1.75. Any of the preceding compositions, wherein the composition further comprises an abrasive (e.g., in addition to any calcium pyrophosphate and/or insoluble sodium metaphosphate);

1.76. Composition 1.75, wherein the abrasive selected from silica (e.g., hydrated silica, precipitated silica), calcium carbonate, calcium orthophosphate, dicalcium orthophosphate, tricalcium phosphate, and arginine carbonate, e.g., in an amount of 0.1 to 10%, or 0.1 to 5%, or 1 to 5%, or 2.5 to 5%;

1.77. Any of the preceding compositions, wherein the composition does not comprise a hydrated silica or precipitated silica abrasive (e.g., synthetic high-cleaning silica)

1.78. Any of the preceding compositions, wherein the composition further comprises a desensitizing agent, e.g., in an amount from 0.1 to 5% by weight, such as potassium nitrate;

1.79. Any of the preceding compositions, wherein the composition further comprises an enamel strengthening agent, e.g., in an amount from 0.1 to 5% by weight, (e.g., zinc phosphate);

1.80. Any of the preceding compositions, wherein the composition does not comprise any acetate esters, for example, wherein the composition does not comprise any of: triacetin, glyceryl acetate, propylene glycol diacetate, ethylene glycol diacetate, and diethylene glycol diacetate;

1.81. Any of the preceding compositions, wherein the composition does not comprise any humectants, for example, wherein the composition does not comprise any of glycerol, propylene glycol, sorbitol, or xylitol;

1.82. Any of the preceding compositions, wherein the composition comprises 1 to 3% of sodium lauryl sulfate, and 0.1 to 0.5% of cocamidopropyl betaine, by weight of the composition;

1.83. Any of the preceding compositions, wherein the composition comprises 1.5 to 2.5% of sodium lauryl sulfate, and 0.2 to 0.4% of cocamidopropyl betaine, by weight of the composition;

1.84. Any of the preceding compositions, wherein the composition comprises about 2% of sodium lauryl sulfate, and about 0.3% of cocamidopropyl betaine, by weight of the composition;

1.85. Any of the preceding compositions, wherein the composition comprises sodium lauryl sulfate and cocamidopropyl betaine in a weight ratio of about 8:1 to 5:1, e.g., about 6:1;

1.86. Any of the preceding compositions, wherein the composition comprises potassium peroxymonosulfate in an amount of 1% to 5%, 20-40% calcium pyrophosphate, and 25-50% of a polyoxyethylene/polyoxypropylene triblock copolymer having the formula HO—[CH$_2$CH$_2$O]$_a$[—CH(CH$_3$)CH$_2$O—]$_b$[CH$_2$CH$_2$O]$_a$—H, wherein an integer between 10 and 12 (e.g., 11), and b is an integer between 15 and 20 (e.g., 16), e.g., the polymer is Pluronic L35, each by weight of the composition;

1.87. Any of the preceding compositions, wherein the composition comprises potassium peroxymonosulfate in an amount of 1% to 3%, 20-30% calcium pyrophosphate, and 25-35% of a polyoxyethylene/polyoxypropylene triblock copolymer having the formula HO—[CH$_2$CH$_2$O]$_a$[—CH(CH$_3$)CH$_2$O—]$_b$[CH$_2$CH$_2$O]$_a$—H, wherein an integer between 10 and 12 (e.g., 11), and b is an integer between 15 and 20 (e.g., 16), e.g., the polymer is Pluronic L35, each by weight of the composition;

1.88. Any of the preceding compositions, wherein the composition further comprises polyvinylpyrrolidone in an amount of 1 to 10%, and PEG/PPG random copolymer having an average molar ratio of ethylene glycol units (EG) to propylene glycol units (PG) of about 105-125 EG to 55-75 PG (e.g., Pluracare L1220 polymer) in an amount of 6 to 15%, and polyethylene glycol 600 in an amount of 5 to 20%, each by weight of the composition;

1.89. Any of the preceding compositions, wherein the composition further comprises 2% to 5% tetrasodium pyrophosphate and 0.5 to 1.5% disodium pyrophosphate, by weight of the composition;

1.90. Any of the preceding compositions, wherein the composition further comprises a blue dye or pigment, e.g., Blue 15 pigment (also known as CI 74160), optionally in an amount of 0.001 to 0.1% by weight of the composition, e.g., 0.01 to 0.08%, or 0.03 to 0.07%, or about 0.05%, by weight of the composition;

1.91. Any of the preceding compositions, wherein the composition comprises or consists of potassium peroxymonosulfate from 0.1-5% (e.g., 1%), calcium pyrophosphate from 21-30% (e.g., 25%), anionic surfactant (e.g., sodium lauryl sulfate) 1-5% (e.g., 2%), zwitterionic surfactant (e.g., cocamidopropyl betaine) 0.1-1% (e.g., 0.3%), and a flavor system comprising a carrier matrix, wherein the carrier matrix comprises a protective coating layer (e.g., comprising maltodextrin or gum arabica) that encapsulates one or more flavor ingredient(s) within the carrier matrix; and wherein the composition comprises less than 4% water by weight of the total composition (e.g., 0% water, i.e., anhydrous) (e.g., from 0.05% to 3.9% water by weight of the total composition).

1.92. Any of the preceding compositions, wherein the composition comprises or consists of:

| Ingredient | Weight % |
| --- | --- |
| Potassium peroxymonosulfate | 0.1-5% (e.g., about 1%) |
| Calcium pyrophosphate | 21-30% (e.g., about 25%) |
| PEG/PPG triblock copolymer (e.g., Pluronic L35) | 25-35% (e.g., about 30-32% or about 31%) |
| Polyvinylpyrrolidone | 1-15% (e.g., about 5%) |
| PEG-PPG random copolymer (e.g., PEG/PPG-116/66) | 6-15% (e.g., about 10%) |
| Polyethylene glycol (e.g., PEG 600) | 10-20% (e.g., about 12.5%) |
| Polyphosphate (e.g., tetrasodium and di sodium pyrophosphates) | 2.5-5% (e.g., about 4%) |
| Anionic Surfactant (e.g., sodium lauryl sulfate) | 1-5% (e.g., about 2%) |
| Zwitterionic Surfactant (e.g., cocamidopropyl betaine) | 0.1-1% (e.g., about 0.3%) |
| Fluoride source (e.g., sodium monofluorophosphate) | 0.1 to 2% (e.g., about 0.75%) |
| Antioxidant (e.g., BHT) | 0 to 0.3% (e.g., about 0.03%) |
| Thickener (e.g., fumed silica) | 2.5-5% (e.g., about 4%) |
| Blue pigment or dye (e.g., Blue 15) | 0.001 to 0.1% (e.g., about 0.05%) |
| Flavor system comprising a carrier matrix, wherein the carrier matrix comprises a protective coating layer (e.g., comprising maltodextrin or gum arabica) that encapsulates one or more flavor ingredient(s) within the carrier matrix | 0.5-5% |
| Total | ca. 100 |

1.93. Any of the preceding compositions, wherein the composition is a dentifrice, e.g., a toothpaste or a tooth gel;

1.94. Any of the preceding compositions, wherein the composition has the consistency of a paste or gel (e.g., not a free-flowing liquid and not a solid, such as a solid powder or pellets);

1.95. Any of the preceding compositions, wherein the composition does not comprise hydrogen peroxide;

1.96. Any of the preceding compositions, wherein the Composition has a squeeze pressure of 0.03 to 0.2 bar, e.g., 0.03 to 0.15 bar, or 0.03 to 0.10 bar, or 0.03 to 0.07 bar, or 0.04 to 0.06 bar, or about 0.05 bar;

1.97. Any of the preceding compositions, wherein the Composition has a viscosity (measured at 1 rpm) of 50,000 to 300,000 cP, e.g., 100,000 to 300,000 cP, or 150,000 to 250,000 cP, or 175,000 to 225,000 cP, or about 200,000 cP;

1.98. Any of the preceding compositions, wherein after up to 3 months of aging at 40° C./65% relative humidity, the Composition retains a squeeze pressure below 0.1 bar and/or a viscosity (at 1 rpm) below 300,000 cP;

1.99. Any of the preceding compositions, wherein the composition loses not more than 10% of its initial active oxygen (AO) content after up to 3 months of aging at 60° C./75% relative humidity;

1.100. Any of the preceding compositions, wherein the composition has a foam volume of at least 100 mL after stirring at 4000 rpm for 120 seconds, e.g., at least 120 mL, or at least 130 mL, or at least 140 mL;

1.101. Any of the preceding compositions, wherein the composition forms a foam having a bubble size ($R_{32}$) of not more than 50 μm after stirring at 4000 rpm for 120 seconds, e.g., less than 45 μm;

1.102. Any of the preceding compositions, wherein the flavor system comprises one or more flavor ingredients having one or more of the following properties: low boiling point (e.g., volatility), mint-like flavor, enhancer function, base coverage, lingering taste, and lingering chemosensate;

1.103. Any of the preceding compositions, wherein the flavor system comprises a flavor selected from the group consisting of: 4-(4-Hydroxyphenyl)butan-2-one (Raspberry ketone), Amyl acetate, Amyl butyrate, Benzyl acetate, Alpha damascene, Beta damascenone, Camphor, Borneol, Geranyl acetate, Geranyl butyrate, Cis-3-hexenol, Cis-3-hexenyl butyrate, Cis-3-hexenyl caproate, Hexyl acetate, Cis-3-hexenyl acetate, Cis-3-jasmone, D-Isomenthone, Delta decalactone, Delta undecalactone, Dihydro anethole, Dihydro mint lactone, Ethyl butyrate, 2-Ethyl-Methyl-Butyrate, Ethyl acetate, Ethyl caproate, Butyl Butyrate, Butyl Acetate, Allyl caproate, Eucalyptol (1,8-cineole), 1,4-Cineole, Eugenyl acetate, Eugenol, Carvyl Acetate, Gamma Hexalactone, Gamma decalactone, Gamma nonalactone, Gamma octalactone, Alpha Ionone, Beta Ionone, D-Menthone, L-Menthone, Menthol, Menthyl acetate, Methyl acetate, Methyl Jasmonate, Methyl salicylate, N-((Ethoxycarbonyl)methyl)-p-menthane-3-carboxamide (WS-5), N-Ethyl-2-isopropyl-5-methylcyclohexane carboxamide (WS-3), (1R,2S,5R)-2-Isopropyl-N-(4-methoxyphenyl)-5-methylcyclohexanecarboxamide (WS-12), N-Ethyl-2-isopropyl-5-methylcyclohexane carboxamide (WS-23), Phenyl ethyl acetate, Phenyl ethyl alcohol, and Piperitone, or any combination thereof;

1.104. Composition 1.103, wherein any one or more of said flavor ingredients is an encapsulated flavor;

1.105. Composition 1.104, wherein any one or more of said flavor ingredients is in the form of a liquid flavor additive (e.g., not encapsulated);

1.106. Any of the preceding compositions, wherein the flavor system comprises one or more flavor ingredients each in an amount of 0.01-60%, or 0.01-50%, or 0.01-40%, or 0.01-30%, or 0.01-20%, or 0.01-10%, or 0.01-6%, or 0.01-5%, or 0.01-4%, or 0.01-3%, or 0.01-2%, or 0.01-1%, or 0.1-60%, or 0.1-50%, or 0.1-40%, or 0.1-30%, or 0.1-20%, or 0.1-10%, or 0.1-5%, or 0.1-4%, or 0.1-3%, or 0.1-2%, or 0.1-1%, or 0.5-60%, or 0.5-50%, or 0.5-40%, or 0.5-30%, or 0.5-20%, or 0.5-10%, or 0.5-6%, or 0.5-5%, or 0.5-4%, or 0.5-3%, or 0.5-2%, or 0.5-1%, or 1-60%, or 1-50%, or 1-40%, or 1-30%, or 1-20%, or 1-10%, or 1-5%, or 10-60%, or 10-50%, or 10-40%, or 10-30%, or 10-20%, or 20-60%, or 20-50%, or 20-40%, or 20-30%, or 30-60%, or 30-50%, or 30-40%, or 40-60%, or 40-50%, or 50-60%, by weight of the flavor system component of the composition.

In one aspect, any of Composition 1.0 et seq. comprises or consists of:

An effective amount of Pluronic L35 (e.g., 25-35%), e.g., an amount effective to stabilize the potassium peroxymonosulfate;

Potassium peroxymonosulfate (e.g., 0.1-5%); and

A flavor system (e.g., 0.5-5%);

wherein the flavor system comprises:

a carrier matrix and wherein the carrier matrix comprises a protective coating layer encapsulating one or more flavor ingredients;

wherein the protective coating layer comprises maltodextrin or gum arabica; and wherein the carrier matrix is provided in an amount effective so that the hydrophilic groups present on the Pluronic L35 do not prematurely dissolve the maltodextrin despite the presence of maltodextrin's alcohol groups.

The compositions of the present disclosure preferably include potassium peroxymonosulfate as a whitening agent, optionally in combination with a second whitening agent, such as hydrogen peroxide (e.g., aqueous hydrogen peroxide or a hydrogen peroxide-polymer complex, such as cPVP-hydrogen peroxide complex).

Potassium peroxymonosulfate (also known as MPS, KMPS, potassium monopersulfate, or potassium monoperoxysulfate) is commercially available as Caroat® or Oxone®, both of which are a triple salt of potassium peroxymonosulfate, potassium hydrogen sulfate and potassium sulfate ($2KHSO_5 \cdot KHSO_4 \cdot K_2SO_4$).

The amount of potassium peroxymonosulfate in the compositions of the invention is effective to result in improved tooth whitening when used once or twice daily for about three months as compared to a control composition without the peroxymonosulfate salt. The amount of peroxymonosulfate salt typically is about 0.1% to about 10%, by weight of the composition, preferably about 1 wt. % or 2 wt. %.

Potassium peroxymonosulfate has limited stability in aqueous solutions and can be stabilized by other common toothpaste ingredients. Therefore, contact with water during processing and storage should be avoided or minimized. The compositions are preferably packaged in a moisture free environment.

As used herein, the term "insoluble sodium metaphosphate" is used to refer to the insoluble polymeric sodium metaphosphate, which has the empirical formula $[NaPO_3]n$, also known as "Maddrell's Salt." This is a highly useful abrasive, which is insoluble in water and has a low capacity for releasing phosphate ion into solution. It has a high molecular weight, with values of n up to 2000. It is distinct from such soluble species as trisodium orthophosphate ($Na_3PO_4$), tetrasodium pyrophosphate ($Na_4P_2O_7$), pentasodium tripolyphosphate ($Na_5P_3O_{10}$), hexasodium tetraphosphate ($Na_6P_4O_{13}$), sodium trimetaphosphate ($Na_3[(PO_3)_3]$), or sodium hexametaphosphate ($Na_6[(PO_3)_6]$), all of which are water soluble and prone to hydrolysis under aqueous conditions to provide orthophosphate anion.

The compositions of the present disclosure contain no water or have a low water content. As used herein, the term "low water content" means the total concentration of water, including any free water and all water contained in any ingredients. In various embodiments of the composition, the amount of water is in an amount of less than 4% by weight, or less than 3% by weight, or less than 2% by weight, or less than 1% by weight, or less than 0.5% by weight, or less than 0.1%, or about 0.0001% to about 4% by weight, or about 0.0001% to about 0.5% by weight or about 0.0001% to about 0.1% by weight. In certain aspects, "low water" may refer to a composition that has no water (e.g., anhydrous) (e.g., 0% water by wt.).

As used herein, an "oral care composition" refers to a composition for which the intended use includes oral care, oral hygiene, and/or oral appearance, or for which the intended method of use comprises administration to the oral cavity, and refers to compositions that are palatable and safe for topical administration to the oral cavity, and for providing a benefit to the teeth and/or oral cavity. The term "oral care composition" thus specifically excludes compositions which are highly toxic, unpalatable, or otherwise unsuitable for administration to the oral cavity. In some embodiments, an oral care composition is not intentionally swallowed, but is rather retained in the oral cavity for a time sufficient to affect the intended utility. The oral care compositions as disclosed herein may be used in nonhuman mammals such as companion animals (e.g., dogs and cats), as well as by humans. In some embodiments, the oral care compositions as disclosed herein are used by humans. Oral care compositions include, for example, dentifrice and mouthwash. In some embodiments, the disclosure provides mouthwash formulations.

In certain aspects, the low water oral care compositions comprise potassium peroxymonosulfate as a whitening agent. In this aspect, the amount of potassium peroxymonosulfate in the compositions of the disclosure is effective to result in improved tooth whitening when used once or twice daily for about three months as compared to a control composition without the peroxymonosulfate salt. The amount of peroxymonosulfate salt typically is about 0.1% to about 10%, by weight of the composition.

In some embodiments, the compositions of the present disclosure, e.g., any of Composition 1.0 et seq., contain a buffering agent. Examples of buffering agents include anhydrous carbonates such as sodium carbonate, sesquicarbonates, bicarbonates such as sodium bicarbonate, silicates, bisulfates, phosphates such as monopotassium phosphate and dipotassium phosphate, citrates, pyrophosphates (sodium and potassium salts) and combinations thereof. The amount of buffering agent is sufficient to provide a pH of about 5 to about 9, preferable about 6 to about 8, and more preferable about 7, when the strip is hydrated. Typical amounts of buffering agent are about 0.1% to about 5%, in one embodiment about 1% to about 3%, in another embodiment about 0.5% to about 1%, by weight of the total composition.

The compositions of the present disclosure, e.g., any of Composition 1.0 et seq., comprise a poloxamer, which is a polyoxyethylene-polyoxypropylene triblock copolymer. The term "poloxamer" or "poloxamer copolymer" refers to a nonionic triblock copolymer composed of a central hydrophobic chain of polyoxypropylene units (a.k.a. poly(propylene oxide) units) flanked by two hydrophilic chains of polyoxyethylene units (e.g., poly(ethylene oxide) units).

Poloxamers have the following chemical structure:

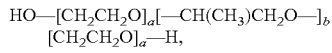

wherein a and b are integers, each typically between 10 and 200. Poloxamers are named according to common conventions based on their molecular weight and ethoxy content, and include poloxamer 407, poloxamer 338, poloxamer 237, poloxamer 188 and poloxamer 124. Pluronic is the name of a line of poloxamer polymers manufactured by BASF. For example, Pluronic F-127 is poloxamer 407. Poloxamers are distinguished from other polyethylene glycol/polypropylene glycol copolymers (PEG/PPG copolymers or EO/PO copolymers) which have a structure other than as a triblock structure, such as a random copolymer structure. Such copolymers that are distinct from poloxamers include the PEG/PPG copolymers sold by BASF as the Pluracare and Pluraflow series polymers, which are random PEG/PPG copolymers.

For example, suitable poloxamers may include one or more of Pluronic® L35, Pluronic® L43, Pluronic® L64, Pluronic® L10, Pluronic® L44, Pluronic® L62, Pluronic® 10R5, Pluronic® 17R4, Pluronic® L25R4, Pluronic® P84, Pluronic® P65, Pluronic® Pl 04, and Pluronic® Pl 05. Pluronic® brand dispersants are commercially available from BASF, Florham Park, N.J.

In some embodiments, the compositions of the present disclosure, e.g., any of Composition 1.0 et seq., may comprise polyvinylpyrrolidone (optionally cross-linked), also known as poly-N-vinyl-poly-2-pyrrolidone, and commonly abbreviated to cross-linked "PVP." PVP generally refers to a polymer containing vinylpyrrolidone (also referred to as N-vinylpyrrolidone, N-vinyl-2-pyrrolidone and N-vinyl-2-pyrrolidinone) as a monomeric unit. The monomeric unit may include a polar imide group, four non-polar methylene groups, and a non-polar methane group. Cross-linked PVP includes those commercially available as KOLLIDON® and LUVICROSS®, marketed by BASF, Mount Olive, N.J., USA; and POLYPLASDO E® INF-10, marketed by, Ashland, Covington, Ky., USA.

The compositions of the present disclosure, e.g., any of Composition 1.0 et seq., contain whitening (oxidizing) agents (e.g., potassium peroxymonosulfate). Whitening agents are generally materials which are effective to provide whitening of a tooth surface to which it is applied, and include agents such as hydrogen peroxide and urea peroxide. In certain aspects, the compositions of the present disclosure, e.g., any of Composition 1.0 et seq., comprise potassium peroxymonosulfate as the whitening agent. In various embodiments, the compositions of the present disclosure may comprise a peroxide whitening agent, comprising a peroxide compound, e.g., wherein no peroxide whitening agents or no peroxide compounds are included. A peroxide compound is an oxidizing compound comprising a bivalent oxygen-oxygen group. Peroxide compounds include peroxides and hydroperoxides, such as hydrogen peroxide, peroxides of alkali and alkaline earth metals, organic peroxy compounds, peroxy acids, pharmaceutically-acceptable salts thereof, and mixtures thereof. Peroxides of alkali and alkaline earth metals include lithium peroxide, potassium peroxide, sodium peroxide, magnesium peroxide, calcium peroxide, barium peroxide, and mixtures thereof. Organic peroxy compounds include carbamide peroxide (also known as urea hydrogen peroxide), glyceryl hydrogen peroxide, alkyl hydrogen peroxides, dialkyl peroxides, alkyl peroxy acids, peroxy esters, diacyl peroxides, benzoyl peroxide, and monoperoxyphthalate, and mixtures thereof. Peroxy acids and their salts include organic peroxy acids such as alkyl peroxy acids, and monoperoxyphthalate and mixtures thereof, as well as inorganic peroxy acid salts such as persulfate, dipersulfate, percarbonate, perphosphate, perborate and persilicate salts of alkali and alkaline earth metals such as lithium, potassium, sodium, magnesium, calcium and barium, and mixtures thereof. In various embodiments, the peroxide compound comprises hydrogen peroxide, urea peroxide, sodium percarbonate and mixtures thereof. In some embodiments, the peroxide compound comprises hydrogen peroxide. In some embodiments, the peroxide compound consists essentially of hydrogen peroxide. In some embodiments, the compositions may comprise a non-peroxide whitening agent. Whitening agents among those useful herein include non-peroxy compounds, such as chlorine dioxide, chlorites and hypochlorites. Chlorites and hypochlorites include those of alkali and alkaline earth metals such as lithium, potassium, sodium, magnesium, calcium and barium. Non-peroxide whitening agents also include colorants, such as titanium dioxide and hydroxyapatite. One or more additional whitening agents are optionally present in a tooth-whitening effective total amount. In some embodiments the compositions additionally comprise an activator, e.g., tetraacetylethylenediamine. In some embodiments, the compositions of the present invention are free of all of the above enumerated additional whitening agents.

In some embodiments, the compositions may comprise a non-oxidative whitening agent. Non-oxidative whitening agents include colorants, such as titanium dioxide and blue pigment or dye, and hydroxyapatite. These agents cause a whiter appearance of the teeth through masking or covering stains, but not chemically removing or destroying the stains.

The compositions of the present disclosure optionally can also include other ingredients, e.g., fillers; surfactants; preservatives, e.g., sodium benzoate and potassium sorbate; color agents including, e.g., dyes and pigments; and sweeteners. In some embodiments, the compositions of the present disclosure comprise one or more surfactants, such as anionic, cationic, zwitterionic or non-ionic surfactants.

As used herein, "anionic surfactant" means those surface-active or detergent compounds that contain an organic hydrophobic group containing generally 8 to 26 carbon atoms or generally 10 to 18 carbon atoms in their molecular structure and at least one water-solubilizing group selected from sulfonate, sulfate, and carboxylate so as to form a water-soluble detergent. Usually, the hydrophobic group will comprise a $C_8$-$C_{22}$ alkyl, or acyl group. Such surfactants are employed in the form of water-soluble salts and the salt-forming cation usually is selected from sodium, potassium, ammonium, magnesium and mono-, di- or tri-$C_2$-$C_3$ alkanolammonium, with the sodium, magnesium and ammonium cations again being the usual ones chosen. Some examples of suitable anionic surfactants include, but are not limited to, the sodium, potassium, ammonium, and ethanolammonium salts of linear $C_8$-$C_{18}$ alkyl ether sulfates, ether sulfates, and salts thereof. Suitable anionic ether sulfates have the formula $R(OC_2H_4)_nOSO_3M$ wherein n is 1 to 12, or 1 to 5, and R is an alkyl, alkylaryl, acyl, or alkenyl group having 8 to 18 carbon atoms, for example, an alkyl group of $C_{12}$-$C_{14}$ or $C_{12}$-$C_{16}$, and M is a solubilizing cation selected from sodium, potassium, ammonium, magnesium and mono-, di- and triethanol ammonium ions. Exemplary alkyl ether sulfates contain 12 to 15 carbon atoms in the alkyl groups thereof, e.g., sodium laureth (2 EO) sulfate. Some preferred exemplary anionic surfactants that may be used in the compositions of the present disclosure include sodium laurel ether sulfate (SLES), sodium lauryl sulfate, and ammonium lauryl sulfate. In certain embodiments, the anionic surfactant is present in an amount of 0.01 to 5.0%, 0.1 to 2.0%, 0.2 to 0.4%, or about 0.33%.

As used herein, "nonionic surfactant" generally refers to compounds produced by the condensation of alkylene oxide groups (hydrophilic in nature) with an organic hydrophobic compound which may be aliphatic or alkyl-aromatic in nature. Examples of suitable nonionic surfactants include poloxamers (sold under trade name PLURONIC®), polyoxyethylene, polyoxyethylene sorbitan esters (sold under trade name TWEENS®), Polyoxyl 40 hydrogenated castor oil, fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, alkyl polyglycosides (for example, fatty alcohol ethers of polyglycosides, such as fatty alcohol ethers of polyglucosides, e.g., decyl, lauryl, capryl, caprylyl, myristyl, stearyl and other ethers of glucose and polyglucoside polymers, including mixed ethers such as capryl/caprylyl ($C_{8-10}$) glucoside, coco ($C_{8-16}$) glucoside, and lauryl ($C_{12-16}$) glucoside), long chain tertiary amine oxides, long chain tertiary phosphine oxides, long chain dialkyl sulfoxides, and mixtures of such materials.

In some embodiments, the nonionic surfactant comprises amine oxides, fatty acid amides, ethoxylated fatty alcohols, block copolymers of polyethylene glycol and polypropylene glycol, glycerol alkyl esters, polyoxyethylene glycol octylphenol ethers, sorbitan alkyl esters, polyoxyethylene glycol sorbitan alkyl esters, and mixtures thereof. Examples of amine oxides include, but are not limited to, laurylamidopropyl dimethylamine oxide, myristylamidopropyl dimethylamine oxide, and mixtures thereof. Examples of fatty acid amides include, but are not limited to, cocomonoethanolamide, lauramide monoethanolamide, cocodiethanolamide, and mixtures thereof. In certain embodiments, the nonionic surfactant is a combination of an amine oxide and a fatty acid amide. In certain embodiments, the amine oxide is a mixture of laurylamidopropyl dimethylamine oxide and myristylamidopropyl dimethylamine oxide. In certain embodiments, the nonionic surfactant is a combination of lauryl/myristylamidopropyl dimethylamine oxide and cocomonoethanolamide. In certain embodiments, the nonionic surfactant is present in an amount of 0.01 to 5.0%, 0.1 to 2.0%, 0.1 to 0.6%, 0.2 to 0.4%, about 0.2%, or about 0.5%.

As used herein, the term "cationic surfactant" includes the cationic surfactants disclosed in WO 2007/011552A2, the contents of which are incorporated herein by reference in its entirety.

Examples of the surfactant that can be used in compositions of the disclosure, e.g., any of Composition 1.0 et seq, are sodium lauryl sulfate, sorbitan fatty acid ester, polyoxyethylene (20) sorbitan monooleate (Polysorbate 80 or Tween 80), polyethylene glycol fatty acid ester, polyoxyethylene sorbitan fatty acid ester, polyoxyethylene alkyl ether, polyoxyethylene polyoxypropylene alkyl ether, polyoxyethylene polyoxypropylene block copolymer, polyoxyethylene alkyl phenyl ether, polyoxyethylene castor oil, polyoxyethylene hydrogenated castor oil, polyoxyethylene sorbitol fatty acid ester and polyoxyethylene glycerol fatty acid ester. In the present invention, each of them may be used solely or two or more thereof may be used jointly. Typical amounts of surfactant are about 0.1% to about 3%, in one embodiment about 0.1% to about 2%, in another embodiment about 0.1% to about 1%, by weight of the total composition.

Examples of the filler are crystalline cellulose, ethylcellulose, dextrin, various kinds of cyclodextrin (α-cyclodextrin, β-cyclodextrin and γ-cyclodextrin), sodium sulfate, as well as derivatives thereof and pullulan.

Useful flavor ingredients or agents that can be used in the flavor system of the disclosed compositions, e.g., any of Composition 1.0 et seq, include natural and synthetic flavoring sources including, e.g., volatile oils, synthetic flavor oils, flavoring aromatics, oils, liquids, oleoresins and extracts derived from plants, leaves, flowers, fruits, stems and combinations thereof. Suitable flavor ingredients or agents include, e.g., citric oils, e.g., lemon, orange, grape, lime and grapefruit, fruit essences including, e.g., apple, pear, peach, grape, strawberry, raspberry, cherry, plum, pineapple, apricot, and other fruit flavors. Other useful flavor ingredients or agents include, e.g., aldehydes and esters (e.g., benzaldehyde (cherry, almond)), citral, i.e., alpha-citral (lemon, lime), neral, i.e., beta-citral (lemon, lime), decanal (orange, lemon), aldehyde C-8 (citrus fruits), aldehyde C-9 (citrus fruits), aldehyde C-12 (citrus fruits), tolyl aldehyde (cherry, almond), 2,6-dimethyloctanal (green fruit), 2-dodedenal (citrus, mandarin) and mixtures thereof.

Each flavor in the composition may be intended to provide a different effect for the consumer. For example, the following functions may be performed by one or more of the flavor ingredients used in the present compositions:

| Function Description | Definition |
|---|---|
| Low Boiling Point | Flavor ingredients, such as esters, that release quickly from the dentifrice matrix upon brushing by nature of their low boiling point (i.e., volatility). These components help to cover the initial off-tastes of the dentifrice and provide a pleasant top-note or first impression to the consumer during brushing. |
| Mint-Like | Flavor ingredients which can be found in natural mint essential oils or which share flavor attributes that can be perceived as minty-like. |
| Enhancer | Flavor ingredients whose attributes help to complement other flavor ingredients/components in the composition to provide a balanced experience. |
| Base Coverage | Flavor ingredients/components whose flavor attributes help to cover the soapy, bitter, and chemical off-notes present during brushing. |
| Lingering Taste | Flavor ingredients/components whose flavor attributes remain after brushing. These components help to mask or cover the soapy, bitter, and chemical off-notes perceived after brushing. |
| Lingering chemosensate | Chemosensory agents such as long-lasting cooling components that remain between 1-45 minutes after brushing. These agents help to focus perception on sensations in the mouth and minimize off-tastes. |

The following flavor ingredients are particularly well-suited to use in the flavor systems according to the present disclosure (ranges are weight percent of the flavor ingredient in the flavor system, and are merely exemplary):

| Flavor ingredient | Function | Range (wt. %) |
|---|---|---|
| 4-(4-Hydroxyphenyl)butan-2-one (Raspberry ketone) | Base coverage & Lingering taste | 0.05%-5% |
| Amyl acetate | Low flashpoint | 0.01%-2% |
| Amyl butyrate | Low flashpoint | 0.01%-2% |
| Benzyl acetate | Low flashpoint | 0.1%-10% |
| Alpha damascene | Base coverage & Lingering taste | 0.01%-2% |
| Beta damascenone | Base coverage & Lingering taste | 0.01%-2% |
| Camphor | Enhancer | 0.05%-10% |
| Borneol | Enhancer | 0.1%-5% |
| Geranyl acetate | Base coverage | 0.1%-5% |
| Geranyl butyrate | base coverage | 0.1%-3% |
| Cis-3-hexenol | Low flashpoint | 0.01%-1% |
| Cis-3-hexenyl butyrate | Low flashpoint | 0.01%-2% |
| Cs-3-hexenyl caproate | Low flashpoint | 0.01%-2% |
| Hexyl acetate | Low flashpoint | 0.01%-2% |
| Cis-3-hexenyl acetate | Low flashpoint | 0.01%-2% |
| Cis-3-jasmone | Base coverage & Lingering taste | 0.01%-3% |
| D-Isomenthone | Mint-like | 0.5%-30% |
| Delta decalactone | Base coverage & Lingering taste | 0.1%-5% |
| Delta undecalactone | Base coverage & Lingering taste | 0.1%-5% |
| Dihydro anethole | Enhancer, Base coverage & Lingering taste | 0.1%-5% |
| Dihydro mint lactone | Base coverage & Lingering taste | 0.1%-5% |
| Ethyl butyrate | Low flashpoint | 0.01%-2% |
| 2-Ethyl-Methyl-Butyrate | Low flashpoint | 0.01%-2% |
| Ethyl acetate | Low flashpoint | 0.01%-2% |
| Ethyl caproate | Low flashpoint | 0.01%-2% |
| Butyl Butyrate | Low flashpoint | 0.01%-2% |
| Butyl Acetate | Low flashpoint | 0.01%-2% |
| Allyl caproate | Low flashpoint | 0.01%-2% |
| Eucalyptol (1,8-cineole) | Enhancer | 0.1%-40% |
| 1,4-Cineole | Enhancer | 0.1%-20% |
| Eugenyl acetate | Enhancer | 0.1%-5% |
| Eugenol | Enhancer | 0.1%-20% |
| Carvyl Acetate | Enhancer | 0.1%-5% |
| Gamma Hexalactone | Base coverage & Lingering taste | 0.1%-5% |
| Gamma decalactone | Base coverage & Lingering taste | 0.1%-5% |
| Gamma nonalactone | Base coverage & Lingering taste | 0.1%-5% |
| Gamma octalactone | Base coverage & Lingering taste | 0.1%-5% |
| Alpha Ionone | Base coverage & Lingering taste | 0.01%-3% |
| Beta Ionone | Base coverage & Lingering taste | 0.01%-3% |
| D-Menthone | Mint-like | 0.5%-50% |
| L-Menthone | Mint-like | 0.5%-50% |
| Menthol | Mint-like | 1%-60% |
| Menthyl acetate | Mint-like | 0.1%-10% |
| Methyl acetate | Low Flashpoint | 0.01%-1% |
| Methyl Jasmonate | Base coverage & Lingering taste | 0.01%-3% |
| Methyl salicylate | Mint-like | 0.1%-50% |
| N-((Ethoxycarbonyl)methyl)-p-menthane-3-carboxamide (WS-5) | Lingering chemosensate | 0.1%-10% |
| N-Ethyl-2-isopropyl-5-methyl-cyclohexane carboxamide (WS-3) | Lingering chemosensate | 0.1%-10% |
| (1R,2S,5R)-2-Isopropyl-N-(4-methoxyphenyl)-5-methylcyclo-hexanecarboxamide (WS-12) | Lingering chemosensate | 0.1%-10% |
| N-Ethyl-2-isopropyl-5-methylcyclo-hexane carboxamide (WS-23) | Lingering chemosensate | 0.1%-10% |
| Phenyl ethyl acetate | Base coverage & Lingering taste | 0.1%-5% |
| Phenyl ethyl alcohol | Base coverage & Lingering taste | 0.1%-5% |
| Piperitone | Mint-like | 0.1%-5% |

Suitable coloring agents include, e.g., food, drug and cosmetic (FD&C) colors including, e.g., dyes, lakes, and certain natural and derived colorants. Useful lakes include dyes absorbed on aluminum hydroxide and other suitable carriers.

Suitable sweetening ingredients or agents that can be used in the flavor system of the disclosed compositions, e.g., any of Composition 1.0 et seq, include stevia, sugars such as sucrose, glucose, invert sugar, fructose, ribose, tagalose, sucralose, maltitol, erythritol, xylitol, and mixtures thereof, saccharin and its various salts (e.g., sodium and calcium salt of saccharin), cyclamic acid and its various salts, dipeptide sweeteners (e.g., aspartame), acesulfame potassium, dihydrochalcone, glycyrrhizin, and sugar alcohols including, e.g., sorbitol, sorbitol syrup, mannitol and xylitol, and combinations thereof.

It is understood that while general attributes of each of the above categories of materials may differ, there may be some common attributes and any given material may serve multiple purposes within two or more of such categories of materials. All of the ingredients in the compositions may have functions in addition to their primary function, and may contribute to the overall properties of the composition, including its stability, efficacy, consistency, mouthfeel, taste, odor and so forth. For example, a binder may also function as a disintegrating agent and vice versa.

In a second aspect, the present disclosure provides a method for whitening teeth comprising the steps of (a) applying Composition 1.0, or any of 1.1 et seq., to the teeth, and (b) maintaining contact of the composition with the teeth for a sufficient period of time (e.g., 0.1 to 60 minutes, or 0.1 to 30 minutes, or 0.1 to 10 minutes, or 0.1 to 5 minutes, or 0.1 to 2 minutes, or 0.1 to 1 minute) to effect whitening of the teeth contacted by the composition. In some embodiments, the composition may be applied using a toothbrush, and the composition maintained in contact with the teeth by using a brushing action. In some embodiments, the composition may be applied to the teeth using a dental tray, and the composition maintained in contact with the teeth by placement of the dental tray in the mouth until whitening is complete.

In other embodiments, the present disclosure provides for the use Composition 1.0, or any of 1.1 et seq., or any other embodiments thereof, for the whitening of the teeth.

In other embodiments, the present disclosure provides for the use Composition 1.0, or any of 1.1 et seq., or any other embodiments thereof, for the distribution of flavor ingredients in the oral cavity upon use of the disclosed oral care compositions.

EXAMPLES

Exemplary embodiments of the present disclosure will be illustrated by reference to the following examples, which are included to exemplify, but not to limit the scope of the present invention.

Example 1: Organoleptic Comparison of Flavor Systems in Oral Care Formulations Typical flavor systems of oral care compositions (liquid peppermint flavor only) are tested against the defined organoleptic criteria defined in Table 1. Oxidized note criteria are listed in Table 2. The organoleptic properties are listed in Table 3. The quality of base coverage performance is ranked on a scale of 0 to 5 by a flavor expert.

TABLE 1

Base Coverage Scores.

| | Base Coverage | Comments |
|---|---|---|
| Score | 5 | Highest organoleptic performance of base coverage, pleasant brushing experience similar to a traditional toothpaste, no underlying tastes of active ingredients, solvents, polymers, etc. No lingering aftertaste. |
| Score | 4 | Pleasant brushing experience. No underlying tastes of active ingredients, solvents, polymers, etc. Slight negative lingering aftertaste from the active ingredient. |
| Score | 3 | Underlying taste of active ingredients, solvents, polymers, etc. are present during brushing. Negative lingering aftertaste from the active ingredient. |
| Score | 2 | Perceivable taste of active ingredients, solvents, polymers, etc. are present during brushing. Negative lingering aftertaste from the formula ingredients. |
| Score | 1 | Minimally pleasant experience with strong taste of active ingredients, solvents, polymers, etc. Negative lingering aftertaste from formula ingredients. |
| Score | 0 | Unpleasant brushing experience, obvious and unpleasant tastes of active ingredients, solvents, polymers, etc. Negative lingering aftertaste from formula ingredients. |

Quality of oxidized taste notes is ranked on a scale of 0 to 5 by a flavor expert. Oxidized taste notes are observed as flavor ingredients are oxidized over time. Oxidized flavors create unpleasant taste attributes and off-tastes in oral care formulas.

TABLE 2

Oxidized Note

| | Oxidized Note | Comments |
|---|---|---|
| Score | 5 | Extreme amount of an oxidized note, sharp, and harsh taste that lingers |
| Score | 4 | High oxidized note, unacceptable |
| Score | 3 | Moderate oxidized note that is borderline acceptable |
| Score | 2 | Perceivable oxidized note that is acceptable |
| Score | 1 | Slight oxidized note that may not be detectable by a non-expert |
| Score | 0 | No perceived oxidized note |

TABLE 3

Comparison of Flavor Systems in Oral Care Formulations:

| | | | Stability | |
|---|---|---|---|---|
| Flavoring System | Organoleptic Criteria | Initial | Control Room Temp | Accelerated Aged Range |
| Toothpaste A (MPS) | Base Coverage: | 3.5 | 2.5 | 2 |
| | Oxidized Notes: | 2.5 | 4 | 4 |
| Toothpaste B (4% HP) | Base Coverage: | 3 | 3 | 2 |
| | Oxidized Notes: | 3 | 3.5 | 4 |

TABLE 4

Toothpaste A Formulation.

| Ingredient | Weight % |
|---|---|
| Potassium peroxymonosulfate | 0.1-5% (e.g., 1%) |
| Calcium pyrophosphate | 21-30% (e.g., 25%) |
| PEG/PPG triblock copolymer (e.g., Pluronic L35) | 25-35% (e.g., 31%) |
| Polyvinylpyrrolidone | 1-15% (e.g., 5%) |
| PEG-PPG random copolymer | 6-15% (e.g., 10%) |
| Polyethylene glycol | 10-20% (e.g., 12.5%) |
| Polyphosphate | 2.5-5% (e.g., 4%) |
| Anionic Surfactant (e.g., sodium lauryl sulfate) | 1-5% (e.g., 2%) |
| Zwitterionic Surfactant (e.g., cocamidopropyl betaine) | 0.1-1% (e.g., 0.3%) |
| Fluoride source | 0.1 to 2% (e.g., 0.75%) |
| Antioxidant | 0 to 0.3% (e.g., 0.03%) |
| Thickener | 2.5-5% (e.g., 4%) |
| Total | ca. 100 |

TABLE 5

Toothpaste B Formulation.

| Ingredients | Weight (%) |
|---|---|
| Humectants (e.g., non-crystal sorbitol, 99.5% vegetable refined glycerin polyhydric alcohols, polyoxyethylene glycols) | 45-60% (e.g., 55%) |
| Abrasives (e.g., high cleaning silica, potassium silicate, perlite, synthetic amorphous silica, synthetic abrasive silica, core shell silica, precipitated silica, precipitated calcium carbonate, dicalcium phosphate, calcium carbonate, sodium bicarbonate) | 10%-20% (e.g., 15%) |
| Thickening Agents (e.g., thickening silica, xanthan gum, | 15%-25% (e.g., 19.5) |

TABLE 5-continued

Toothpaste B Formulation.

| Ingredients | Weight (%) |
|---|---|
| gums, carbomers, carrageenans, sodium carboxymethyl cellulose, polyanionic cellulose, fumed silica) | |
| Foam Modulator (e.g., sodium lauroyl sarcosinate, sodium lauryl sulfate powder, sodium lauryl sulfate liquid, polyethylene glycols) | 1%-5% (e.g., 2%) |
| Stain Prevention Agents (e.g., tetrasodium pyrophosphate, disodium pyrophosphate, sodium tripolyphosphate, sodium hexametaphosphate, zinc citrate) | 0.5%-2.5% (e.g., 1.3%) |
| Anticalculus/Anti tartar Agents (e.g., stannous ion sources, poly-carboxylate polymers, polyamino-propane sulfonic acid, azacycloalkane-2,2-diphosphonates, tetrasodium pyro-phosphates, calcium pyrophosphate, alumina, dicalcium orthophosphate dihydrate, n-calcium pyrophosphate, tricalcium phosphate, calcium polymeta-phosphate, insoluble sodium polymetaphosphate) | 0.5-2.5% (e.g., 1.30) |
| Anticariogenic Agents (e.g., fluoride ion sources, stannous ion sources, xylitol, sodium monofluoro-phosphate) | 0.5%-2% (e.g., 0.8) |
| Hydrogen Peroxide | 1%-5% (e.g., 4%) |
| Nutrients, Colorants, Flavoring agents, Saliva stimulating source, Desensitizing agents, Preservatives, Antioxidants, Water, pH Modifiers | q.s. |

Example 2: Evaluation of the Flavor System of the Invention Using a Maltodextrin-Based Flavor Encapsulate The following tables describe studies which examine the organoleptic results for a variety of flavoring systems in accelerated aging studies.

TABLE 6

Initial and Accelerated Aged Organoleptic Results for the Flavor System (Herbal Liquid Flavor + Peppermint Maltodextrin Encapsulate) in Toothpaste A.

| Flavoring System | Organoleptic Criteria | Initial | Mid-Point Control Room Temp | Mid-Point Accelerated Aged Temp | Final Aged Control Room Temp | Final Aged Accelerated Aged Temp |
|---|---|---|---|---|---|---|
| Sample 1 Liquid Flavor | Base Coverage: | 3 | 3 | 3 | 2.5 | 3 |
| | Oxidized Notes: | 2.5 | 2.5 | 2.5 | 2.5 | 3 |
| Sample 2 Liquid Flavor + Low Dosage Encapsulate | Base Coverage: | 3.5 | 3.5 | 3.5 | 3 | 3.5 |
| | Oxidized Notes: | 1.5 | 1.5 | 1.5 | 2.5 | 3 |
| Sample 3 Liquid Flavor + High Dosage Encapsulate | Base Coverage: | 4 | 4 | 4 | 3.5 | 4 |
| | Oxidized Notes: | 1 | 1 | 1 | 1.5 | 1 |
| Sample 4 Liquid Flavor + Low Dosage (No encapsulation) | Base Coverage: | 3 | 3 | 2.5 | 2 | 2 |
| | Oxidized Notes: | 2 | 3.5 | 3.5 | 4 | 4 |
| Sample 5 Liquid Flavor + High Dosage (No encapsulation) | Base Coverage: | 3 | 3.5 | 3 | 3 | 3 |
| | Oxidized Notes: | 1.5 | 2.5 | 2.5 | 5 | 5 |
| Sample 6 High Dosage Encapsulate | Base Coverage: | 2 | 2 | 2 | 1 | 1 |
| | Oxidized Notes: | 1 | 1 | 1 | 1 | 1 |
| Sample 7 High Dosage (No encapsulation) | Base Coverage: | 2 | 2 | 0 | 0 | 0 |
| | Oxidized Notes: | 5 | 5 | 5 | 5 | 5 |

TABLE 7

Initial and Accelerated Aging Organoleptic Results for the Flavor System (Herbal Liquid Flavor + Peppermint Maltodextrin Encapsulate) in Toothpaste B.

| Flavoring System | Organoleptic Criteria | Initial | Mid-Point Control Room Temp | Mid-Point Accelerated Aged Temp | Final Aged Control Room Temp | Final Aged Accelerated Aged Temp |
|---|---|---|---|---|---|---|
| Sample 8 Liquid Flavor | Base Coverage: | 3.5 | 3.5 | 3.5 | 3.5 | 3.5 |
| | Oxidized Notes: | 0 | 0 | 0 | 0 | 0 |
| Sample 9 | Base Coverage: | 4 | 4 | 4 | 4 | 4 |

TABLE 7-continued

Initial and Accelerated Aging Organoleptic Results for the Flavor System (Herbal Liquid Flavor + Peppermint Maltodextrin Encapsulate) in Toothpaste B.

| | | | Mid-Point | | Final Aged | |
|---|---|---|---|---|---|---|
| Flavoring System | Organoleptic Criteria | Initial | Control Room Temp | Accelerated Aged Temp | Control Room Temp | Accelerated Aged Temp |
| Liquid Flavor + Low Dosage Encapsulate | Oxidized Notes: | 0 | 0 | 0 | 0 | 0 |
| Sample 10 | Base Coverage: | 4.5 | 4.5 | 4.5 | 4.5 | 4.5 |
| Liquid Flavor + High Dosage Encapsulate | Oxidized Notes: | 0 | 0 | 0 | 0 | 0 |
| Sample 11 | Base Coverage: | 3.5 | 3.5 | 3.5 | 3.5 | 3.5 |
| Liquid Flavor + Low Dosage (No encapsulation) | Oxidized Notes: | 2 | 4 | 4.5 | 4 | 4.5 |
| Sample 12 | Base Coverage: | 3.5 | 3.5 | 3.5 | 3.5 | 3.5 |
| Liquid Flavor + High Dosage (No encapsulation) | Oxidized Notes: | 2 | 4 | 4.5 | 4 | 5 |
| Sample 13 | Base Coverage: | 1 | 1 | 0 | 1 | 0 |
| High Dosage Encapsulate | Oxidized Notes: | 0 | 0 | 0 | 0 | 0 |
| Sample 14 | Base Coverage: | 1 | 1 | 0 | 1 | 0 |
| High Dosage (No encapsulation) | Oxidized Notes: | 2 | 4 | 4.5 | 4 | 5 |

Example 3: Evaluation of the Flavor System of the Invention Using a Gum Arabica Based Flavor Encapsulate

TABLE 8

Initial and Accelerated Aging Organoleptic Results for the Flavor System (Mint Liquid Flavor + Peppermint Gum Arabica Encapsulate) in Toothpaste A.

| | | | Mid-Point | | Final Aged | |
|---|---|---|---|---|---|---|
| Flavoring System | Organoleptic Criteria | Initial | Control Room Temp | Accelerated Aged Temp | Control Room Temp | Accelerated Aged Temp |
| Sample 15 Liquid Flavor | Base Coverage: | 4 | 4 | 3.5 | 4 | 3.5 |
| | Oxidized Notes: | 1 | 1 | 2 | 1.5 | 2 |
| Sample 16 Liquid Flavor + Low Dosage Encapsulate | Base Coverage: | 4.5 | 4.5 | 4 | 4.5 | 4 |
| | Oxidized Notes: | 1 | 1 | 1.5 | 1 | 2 |
| Sample 17 Liquid Flavor + High Dosage Encapsulate | Base Coverage: | 4.5 | 4.5 | 4 | 4.5 | 4 |
| | Oxidized Notes: | 2 | 1 | 1.5 | 1 | 2 |
| Sample 18 Liquid Flavor + Low Dosage (No encapsulation) | Base Coverage: | 4 | 4 | 4 | 3.5 | 3 |
| | Oxidized Notes: | 2 | 2 | 2.5 | 2.5 | 3 |
| Sample 19 Liquid Flavor + High Dosage (No encapsulation) | Base Coverage: | 4 | 4.5 | 4 | 3.5 | 2.5 |
| | Oxidized Notes: | 2.5 | 3 | 3.5 | 3.5 | 4 |
| Sample 20 High Dosage Encapsulate | Base Coverage: | 4 | 3.5 | 3 | 3 | 3 |
| | Oxidized Notes: | 1 | 1.5 | 2.5 | 2.5 | 3 |
| Sample 21 High Dosage (No encapsulation) | Base Coverage: | 3.5 | 3.5 | 3.5 | 3.5 | 3 |
| | Oxidized Notes: | 2 | 2 | 2.5 | 2 | 3 |
| Sample 22 Low Dosage | Base Coverage | 2.5 | 2.5 | 2 | 2 | 1.5 |

TABLE 8-continued

Initial and Accelerated Aging Organoleptic Results for the Flavor System (Mint Liquid Flavor + Peppermint Gum Arabica Encapsulate) in Toothpaste A.

| Flavoring System | Organoleptic Criteria | Initial | Mid-Point Control Room Temp | Mid-Point Accelerated Aged Temp | Final Aged Control Room Temp | Final Aged Accelerated Aged Temp |
|---|---|---|---|---|---|---|
| Encapsulation | Oxidized Notes | 3 | 3 | 3.5 | 3.5 | 4 |
| Sample 23 Low Dosage (No Encapsulation) | Base Coverage | 2 | 2 | 2 | 2 | 1.5 |
| | Oxidized Notes | 3 | 3.5 | 4 | 4 | 4.5 |

TABLE 9

Initial and Accelerated Aging Organoleptic Results for the Flavor System (Wintergreen Liquid Flavor + Peppermint Gum Arabica Encapsulate) in Toothpaste A.

| Flavoring System | Organoleptic Criteria | Initial | Mid-Point Control Room Temp | Mid-Point Accelerated Aged Temp | Final Aged Control Room Temp | Final Aged Accelerated Aged Temp |
|---|---|---|---|---|---|---|
| Sample 24 Liquid Flavor | Base Coverage: | 4.5 | 4.5 | 4.5 | 4.5 | 4 |
| | Oxidized Notes: | 1 | 1 | 1.5 | 1 | 1.5 |
| Sample 25 Liquid Flavor + Low Dosage Encapsulate | Base Coverage: | 5 | 5 | 4.5 | 4.5 | 4.5 |
| | Oxidized Notes: | 0.5 | 0.5 | 1 | 1 | 1.5 |
| Sample 26 Liquid Flavor + High Dosage Encapsulate | Base Coverage: | 5 | 5 | 4.5 | 4.5 | 4.5 |
| | Oxidized Notes: | 1 | 1 | 1.5 | 1.5 | 2 |
| Sample 27 Liquid Flavor + Low Dosage (No encapsulation) | Base Coverage: | 4.5 | 4.5 | 4.5 | 4.5 | 4.5 |
| | Oxidized Notes: | 1.5 | 1.5 | 2.5 | 2 | 2.5 |
| Sample 28 Liquid Flavor + High Dosage (No encapsulation) | Base Coverage: | 4.5 | 4 | 4 | 4 | 4 |
| | Oxidized Notes: | 2.5 | 2.5 | 3 | 3 | 4 |
| Sample 29 High Dosage Encapsulate | Base Coverage: | 4 | 3.5 | 3 | 3 | 3 |
| | Oxidized Notes: | 1 | 1.5 | 2.5 | 2.5 | 3 |
| Sample 30 High Dosage (No encapsulation) | Base Coverage: | 3.5 | 3.5 | 3.5 | 3.5 | 3 |
| | Oxidized Notes: | 2 | 2 | 2.5 | 2 | 3 |

Testing of the formulas within the scope of the disclosure demonstrates that they provide improved stability and retained active oxygen activity compared to comparative formulas not within the scope of the present disclosure.

Example 3: Consumer Study

A consumer study is conducted to evaluate consumer preference for three compositions according to the present disclosure. The tested compositions have the following formulas:

| | Formula A | Formula B | Formula C |
|---|---|---|---|
| POTASSIUM CAROATE (45% KMPS) | 2.2 | 2.2 | 2.2 |
| Polyoxypropylene-Polyoxyethylene Block Copolymer | 30.75 | 30.25 | 30.6 |
| CALCIUM PYROPHOSPHATE | 25 | 25 | 25 |
| Thickener (Fumed Silica) | 4 | 4 | 4 |
| SODIUM ACID PYROPHOSPHATE | 1 | 1 | 1 |
| SODIUM MONOFLUOROPHOSPHATE | 1.1 | 1.1 | 1.1 |
| CI PIGMENT BLUE 15 | 0 | 0 | 0.05 |
| POLYETHYLENE GLYCOL 600 | 12.5 | 12.5 | 12.5 |
| TETRASODIUM PYROPHOSPHATE | 3 | 3 | 3 |
| PEG/PPG Random Copolymer (116/66 Copolymer) | 10 | 10 | 10 |
| Polyvinyl pyrrolidone | 5 | 5 | 5 |
| Cocamidopropyl Betaine | 0.3 | 0.3 | 0.3 |
| SODIUM LAURYL SULFATE POWDER | 2 | 2 | 2 |
| SODIUM SACCHARIN | 0.6 | 0.6 | 0.7 |
| SUCRALOSE | 0.05 | 0.05 | 0.05 |
| ENCAPSULATED PEPPERMINT FLAVOR | 0.5 | 0.5 | 0.5 |
| Majesty Infusion Flavor | 0 | 0 | 2 |

|  | Formula A | Formula B | Formula C |
|---|---|---|---|
| MPS No. 8 Flavor | 2 | 0 | 0 |
| Cool Mint masking flavor | 0 | 2.5 | 0 |

Each composition has 0.5 wt. % of encapsulated peppermint flavor. In addition, each of the three compositions has a second non-encapsulated liquid flavor in either 2 wt. % or 2.5 wt. %. Flavor compositions comprising some of ingredients that have some of the preferred flavor functions (low boiling point, mint-like, enhancer, base coverage, lingering taste, and lingering chemosensate) are tested to measure consumer liking and perception of efficacy. The following results are obtained:

| | Results | | |
|---|---|---|---|
| | Flavor System A n = 108 % | Flavor System B n = 122 % | Flavor System C n = 150 % |
| After First Use | | | |
| Overall Opinion: Like a Lot | 32 | 30 | 43 |
| Purchase Intention: Definitely would buy | 25 | 23 | 31 |
| Flavor Liking: Like a lot | 22 | 22 | 35 |
| After 14 Days Usage | | | |
| Overall Opinion: Like a lot | 29 | 32 | 41 |
| Purchase Intention: Would buy | 58 | 55 | 64 |
| Better than usual: whitening toothpaste | 49 | 50 | 57 |
| Noticed whiter teeth | 61 | 61 | 67 |
| Flavor: Liking Like a lot | 20 | 21 | 30 |
| Aftertaste liking: Like a lot | 15 | 18 | 24 |

The results demonstrate that for all three formulas tested, the percentage of consumers who indicated that they would buy the product increased from when they were asked after the first use, and when they were asked after 14 days of use. This strongly shows that the formulas are consumer-friendly. In addition, the results show that the percentage of consumers giving positive marks for all questions asked is significantly higher for the Flavor System C, compared to Flavor System A or B.

The invention has been described above with reference to illustrative Examples, but it is to be understood that the invention is not limited to the disclosed embodiments. Alterations and modifications that would occur to one of skill in the art upon reading the specification are also within the scope of the invention, which is defined in the appended claims.

What is claimed is:

1. A low-water oral care composition comprising:
 (a) a flavor system, wherein the flavor system comprises a carrier matrix for encapsulating one or more flavor ingredient(s), and wherein the carrier matrix comprises a protective coating layer that encapsulates the flavor ingredient(s), and wherein the protective coating layer comprises maltodextrin, and an emulsifier; and
 (b) potassium peroxymonosulfate; and
 wherein the low-water oral care composition comprises less than 4% water by weight of the total composition.

2. The composition of claim 1, wherein the emulsifier is soya lecithin.

3. The composition of claim 1, wherein the composition is anhydrous.

4. The composition of claim 1, wherein the flavor system is present from 0.05% to 5% by weight, relative to the total weight of the composition.

5. The composition of claim 1, wherein the protective layer further comprises a carbohydrate material selected from the group consisting of: corn syrup, a chemically modified starch, a hydrogenated starch hydrolysate, succinylated starch, hydrolyzed starch, and combinations thereof.

6. The composition of claim 1, wherein the carrier matrix further comprises one or more sugars selected from the group consisting of: sucrose, glucose, lactose, fructose, sorbitol, isomalt, ribose, levulose, mannitol, lactitol, xylitol, dextrose, maltitol, xylose, galactose, pentatol, pentose, arabinose and combinations thereof.

7. The composition of claim 1, wherein the protective layer of the carrier matrix consists of agar, maltodextrin, an emulsifier, and optionally sucrose.

8. The composition of claim 1, wherein the maltodextrin is present from 70% to 85% by weight relative the dry weight of the carrier matrix, wherein the emulsifier is present from 0.25 to 2% by weight relative to the dry weight of the carrier matrix, and wherein the agar is present from 0.25% to 2% by weight relative to the dry weight of the carrier matrix.

9. The composition of claim 1, wherein the protective layer comprises maltodextrin, agar, an emulsifier, and sucrose, wherein the maltodextrin is present from 35% to 50% by weight relative the dry weight of the carrier matrix, wherein the emulsifier is present from 0.25 to 2% by weight relative to the dry weight of the carrier matrix, wherein the sucrose is present from 35% to 50% by weight relative the dry weight of the carrier matrix, and wherein the agar is present from 0.25% to 2% by weight relative to the dry weight of the carrier matrix ;.

10. The composition of claim 1, wherein the protective coating layer further comprises qum arabica.

11. The composition of claim 1, wherein the flavor system comprises one or more non-encapsulated liquid flavor ingredients and a carrier matrix that encapsulates one or more additional flavor ingredient(s).

12. The composition of claim 1, wherein the composition further comprises hydrogen peroxide.

13. The composition of claim 1, wherein the composition further comprises a polyoxyethylene/polyoxypropylene triblock copolymer, and wherein the triblock copolymer has the formula:

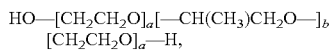

wherein a is an integer between 1 and 30, b is an integer between 10 and 60.

14. The composition of claim 1, wherein the composition further comprises one or more of polyvinylpyrrolidone, polyethylene glycol/polypropylene glycol random copolymer, polyethylene glycol, polyphosphates, and surfactants.

15. The composition of claim 1, wherein the composition further comprises a mixture of anionic and zwitterionic surfactants.

16. The composition of claim 15, wherein the composition comprises 2 to 4% of sodium lauryl sulfate, and 0.1 to 1% of cocamidopropyl betaine, by weight of the composition.

17. The composition of claim 1, wherein the composition comprises or consists of potassium peroxymonosulfate from 0.1-5%, calcium pyrophosphate from 21-30%, 1-5% sodium lauryl sulfate, 0.1-1% cocamidopropyl betaine, and a flavor system comprising a carrier matrix, wherein the carrier matrix comprises a protective coating layer comprising maltodextrin, agar, and an emulsifier, which encapsulates one or more flavor ingredient(s) within the carrier matrix; and wherein the composition comprises less than 1% water by weight of the total composition.

18. The composition of claim 1, wherein the composition comprises or consists of 25-35% of poloxamer 407, 0.1-5% potassium peroxymonosulfate, and 0.5-5% of a flavor system, wherein the flavor system comprises a carrier matrix and wherein the carrier matrix comprises a protective coating layer encapsulating one or more flavor ingredients, and wherein the protective coating layer comprises maltodextrin, agar, and an emulsifier; and wherein the carrier matrix is provided in an amount effective so that the hydrophilic groups present on the poloxamer 407 do not prematurely dissolve the maltodextrin despite the presence of maltodextrin's alcohol groups.

19. A method for whitening teeth comprising the steps of (a) applying a composition according to claim 1, to the teeth, and (b) maintaining contact of the composition with the teeth for a sufficient period of time to effect whitening of the teeth contacted by the composition.

20. The composition according to claim 7, wherein the emulsifier is soya lecithin.

* * * * *